(12) United States Patent
Shivji (10) Patent No.: US 7,976,792 B2
(45) Date of Patent: Jul. 12, 2011

(54) BIOLOGICAL SPECIMEN COLLECTION CARD

(76) Inventor: Ally Shivji, Burnaby (CA)

( * ) Notice: Subject to any disclaimer, the term of this patent is extended or adjusted under 35 U.S.C. 154(b) by 922 days.

(21) Appl. No.: 11/755,605

(22) Filed: May 30, 2007

(65) Prior Publication Data

US 2008/0299010 A1 Dec. 4, 2008

(51) Int. Cl.
*G01N 21/75* (2006.01)
*G01N 31/22* (2006.01)
*G01N 33/52* (2006.01)

(52) U.S. Cl. ........ 422/409; 422/401; 422/420; 422/421; 422/422; 422/423; 422/560; 436/66; 436/169

(58) Field of Classification Search .................... 422/56, 422/58, 401, 409, 420, 421, 422, 423, 560; 436/169, 66
See application file for complete search history.

(56) References Cited

U.S. PATENT DOCUMENTS

| | | | |
|---|---|---|---|
| 3,990,850 A | 11/1976 | Friedman et al. | |
| 4,055,394 A | 10/1977 | Friedman et al. | |
| 4,123,701 A | 10/1978 | Josefsen et al. | |
| 4,225,557 A | 9/1980 | Hartl et al. | |
| 4,365,970 A | 12/1982 | Lawrence et al. | |
| 4,789,629 A | 12/1988 | Baker et al. | |
| 5,100,619 A | 3/1992 | Baker et al. | |
| 5,264,181 A | 11/1993 | Schreiber | |
| 5,273,888 A * | 12/1993 | Guadagno | 435/28 |
| 5,427,953 A | 6/1995 | Yee | |
| 5,747,351 A | 5/1998 | Hemmati | |
| 5,866,007 A | 2/1999 | Whitson et al. | |
| 5,939,252 A | 8/1999 | Lennon et al. | |
| 6,033,627 A | 3/2000 | Shields et al. | |
| 6,077,711 A | 6/2000 | Singer | |
| 6,271,046 B1 * | 8/2001 | Chandler | 436/530 |
| 6,326,214 B1 | 12/2001 | Liu et al. | |
| 6,379,318 B1 | 4/2002 | Nishimura et al. | |

* cited by examiner

*Primary Examiner* — Lyle Alexander
*Assistant Examiner* — Dennis M White
(74) *Attorney, Agent, or Firm* — Cameron IP (57) ABSTRACT

A biological specimen collection card comprises a specimen retaining panel, a rear panel, and a cover panel. There is an opening in the specimen retaining panel for retaining an absorbent insert which is to be impregnated with a biological specimen. The absorbent insert is exposed on both sides of the specimen retaining panel when the absorbent insert is retained in the opening. The rear panel is angularly spaced apart from the specimen retaining panel when the collection card is in an open configuration to facilitate drying of the biological specimen. The cover panel is movable between a first position and a second position. The collection card is in the open configuration when the cover panel is in the first position, and the collection card is in a closed configuration when the cover panel is in the second position. The cover panel covers the absorbent insert when the absorbent insert is retained in the opening and the collection card is in the closed position.

10 Claims, 7 Drawing Sheets

BIOLOGICAL SPECIMEN COLLECTION CARD

BACKGROUND OF THE INVENTION

1. Field of the Invention

The present invention relates to biological specimen collection and, in particular, to a biological specimen collection card.

2. Description of the Related Art

It is well known to use a biological specimen collection card in the form of a blood collection card to collect and transport a blood sample. Typically, a patient's fingertip is punctured and the card is impregnated with blood from the puncture site. The blood is allowed to dry and the card is then sent to a testing center. At the testing center a portion of the card impregnated with blood is cut out, or punched out, and the blood is eluted therefrom. The eluted blood may then be analyzed for evidence of disease or illicit drug use.

In conventional collection cards an exposed surface of the card is impregnated with blood. The blood sample may therefore become contaminated or otherwise damaged during transport. To overcome this problem improved collection cards comprise a protective housing. For example, collection cards used in the HIV and Hepatitis C Home Test Systems available from the Home Access Health Corporation of 2401 West Hassell Road, Suite 1510 Hoffman Estates, Illinois 60169, and sold under the trademark HOME ACCESS, comprise a matchbook type housing. Similar housing is commonly used to transport biological specimens as disclosed in U.S. Pat. No. 4,225,557 to Hartl et al. and U.S. Pat. No. 4,789,629 to Baker et al. However, the use of such packing increases production costs. It is also still necessary to cut out or, punch out, the portion of the card that is impregnated with blood.

BRIEF SUMMARY OF THE INVENTION

It is an object of the present invention to provide an improved biological specimen collection card.

According to a first aspect of the invention there is provided a biological specimen collection card for collecting and transporting a biological specimen. The collection card is movable between an open configuration in which the biological specimen is exposed and a closed configuration in which the biological specimen is covered. The collection card comprises a specimen retaining panel, a rear panel, and a cover panel. There is an opening in the specimen retaining panel for retaining an absorbent insert which is to be impregnated with the biological specimen. The absorbent insert is exposed on both sides of the specimen retaining panel when the absorbent insert is retained in the opening. The rear panel is angularly spaced apart from the specimen retaining panel when the collection card is in the open configuration to facilitate drying of the biological specimen. The cover panel is movable between a first position and a second position. The collection card is in the open configuration when the cover panel is in the first position, and the collection card is in the closed configuration when the cover panel is in the second position. The cover panel covers the absorbent insert when the absorbent insert is retained in the opening and the collection card is in the closed position. The collection card may also include means for retaining the cover panel in the second position.

According to a second aspect of the invention there is provided blank for forming a biological specimen collection card. The blank has a first end and second end opposite to the first end. First and second edges of the blank extend between the ends thereof. The first edge is opposite to the second edge. Spaced apart first and second lines of weakening extend between the edges of the blank. There is an opening in the blank for retaining an absorbent insert which is to be impregnated with the biological specimen. A specimen retaining panel of the collection card is defined between the first end of the blank and the first line of weakening. A rear panel of the collection card is defined between the first line of weakening and the second line of weakening. A cover panel of the collection card is defined between the second line of weakening and the second end of the blank.

The present invention offers the advantage of providing an improved biological specimen card which is economical to manufacture and which does not require a portion of the card impregnated with blood to be cut out, or punched out, prior to the blood sample being analyzed.

DESCRIPTION OF THE PREFERRED EMBODIMENTS

Figure 1:
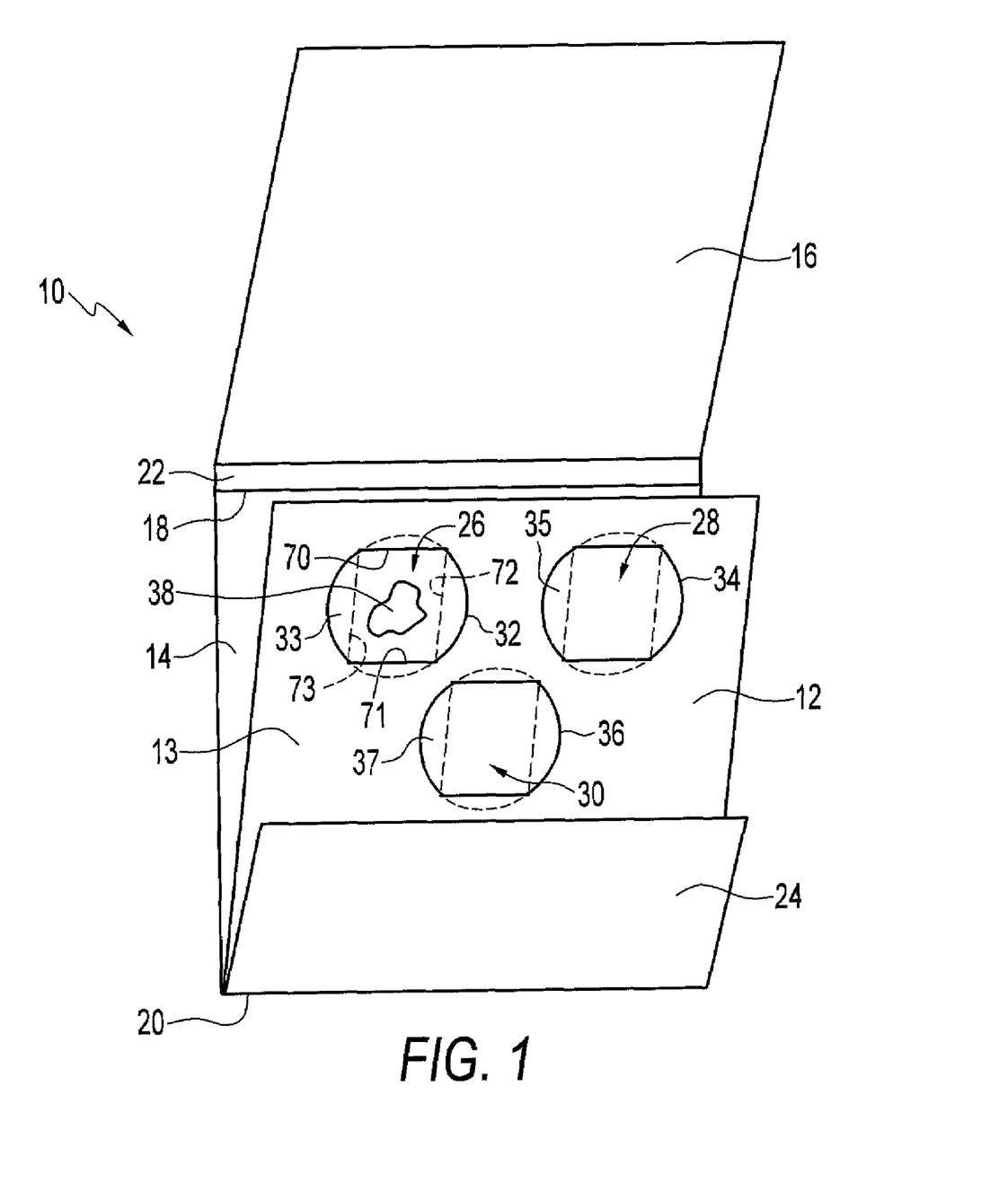
FIG. 1 is a front perspective view of a biological specimen collection card, according to a first embodiment, shown in an open configuration.
Figure 2:
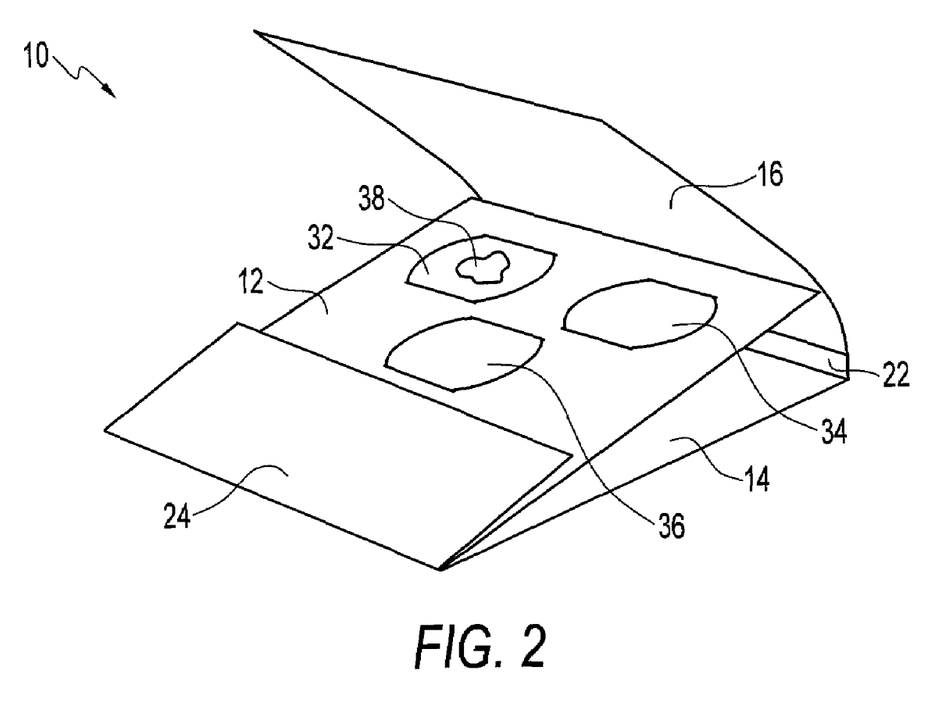
FIG. 2 is a side perspective view of the biological specimen collection card of FIG. 1 shown in the open configuration.
Figure 3:
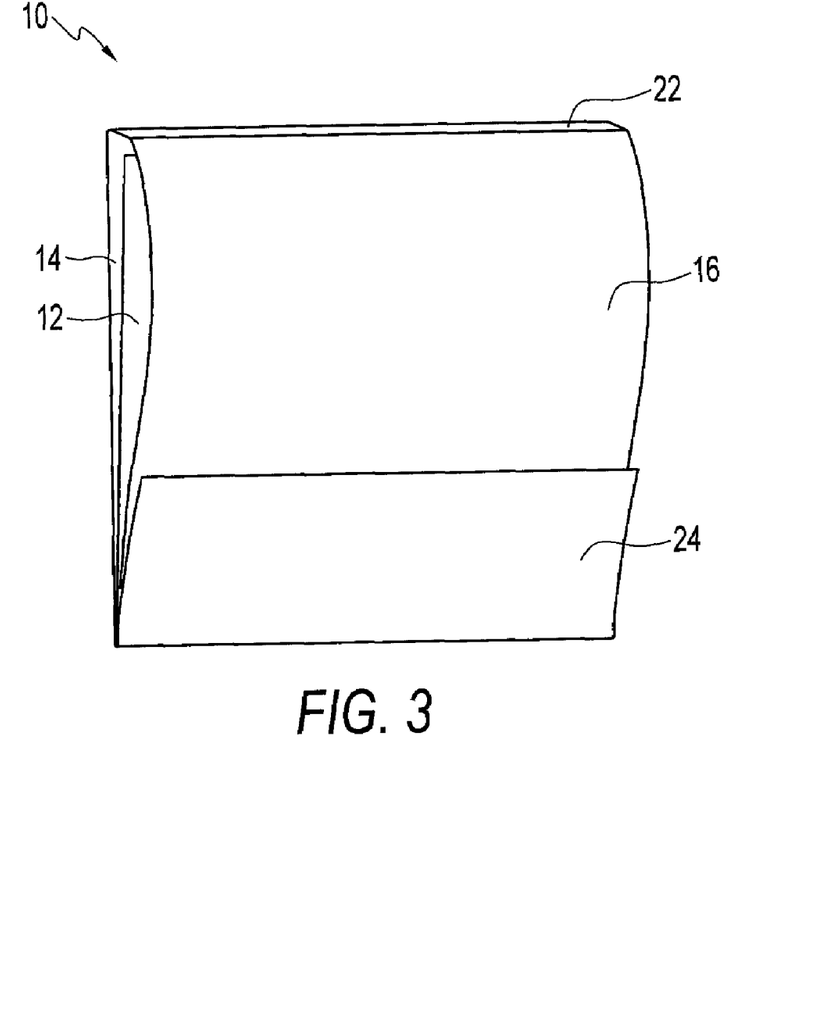
FIG. 3 is a front perspective view of the biological specimen collection card of FIG. 1 shown in a closed configuration.
Figure 4:
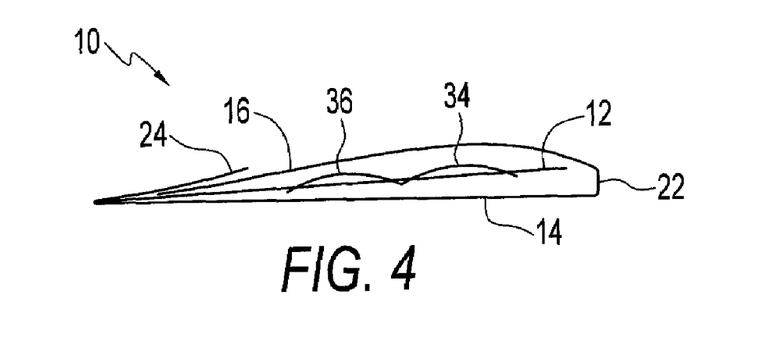
FIG. 4 is a side elevationview of the biological specimen collection card of FIG. 1 shown in the closed configuration.

Referring to the drawings and first to FIGS. 1 to 4, a biological specimen collection card in the form of a blood collection card 10 is shown according to a first embodiment of the invention. The blood collection card 10 is movable between an open configuration and a closed configuration. FIGS. 1 and 2 show the blood collection card 10 in the open configuration. FIGS. 3 and 4 show the blood collection card 10 in the closed configuration.

Referring back to FIG. 1, the blood collection card 10 generally comprises a specimen retaining panel 12, a rear panel 14, and a front cover panel 16. The rear panel 14 has a first edge 18 and a second edge 20 opposite to the first edge 18. A web 22 connects the cover panel 16 to the first edge 18 of the rear panel 14. The specimen retaining panel 12 is connected to the rear panel 14 by an adhesive (not shown). There is a flap 24 disposed along the second edge 20 of the rear panel 14. Openings 26, 28, and 30 in the specimen retaining panel 12 retain absorbent inserts 32, 34, and 36, respectively.

In this example, the openings 26, 28, and 30 are quadrilateral and the absorbent inserts 32, 34, and 36 are circular. However, in other embodiments, the openings and inserts may assume other shapes. As shown for one of the openings 26, the opening 26 has a first pair of opposed edges 70 and 71 and a second pair of opposed edges 72 and 73. The corresponding absorbent insert 32 engages opposed edges 70 and 71 of the opening 26. When retained in the openings, each absorbent insert is exposed on both sides of the specimen retaining panel 12, i.e. both sides of each absorbent insert is exposed. In FIG. 1, only a first side 13 of the specimen retaining panel 12 and a first side 33, 35, and 37 of each absorbent insert 32, 34, and 36, respectively, is shown. A second side of the specimen retaining panel 12 and a second side of each absorbent insert are opposite to the first sides thereof Each absorbent insert 32, 34, and 36 may be impregnated with a blood sample. In this example, only one of the absorbent inserts 32 is impregnated with a blood sample 38.

The removable absorbent inserts 32, 34, and 36 are comprised of materials to suit the requirements of a particular application. For example, the absorbent inserts 32, 34, and 36 may be formed from a material designed to retain a high sample volume. Alternatively, the absorbent inserts 32, 34, and 36 may be formed from a material which selectively retains components of a sample, or the absorbent inserts 32, 34, and 36 may be impregnated with a stabilizer or diagnostic reagent. This flexibility in selecting the type of insert used allows the blood collection card 10 to be used in a variety of applications. Suitable inserts are available from the Whatman International Ltd., of 27 Great West Road, Brentford, Middlesex, United Kingdom TW8 9BW.

As best shown in FIG. 2, when the blood collection card 10 is in the open configuration, the specimen retaining panel 12 is angularly spaced apart from the rear panel 14 exposing both sides of each absorbent insert 32, 34, and 36 to the environment. This facilitates drying of the blood sample 38. This is an important feature because drying of the blood sample 38 imparts stability to components of the blood sample 38 that are measured during analysis. When the blood sample 38 is dry, the cover panel 16 is moved from a first position shown in FIG. 2 to a second position shown in FIG. 3. The blood collection card 10 is in the open configuration when the cover panel 16 is in the first position, and the blood collection card 10 is in the closed configuration when the cover panel 16 is in the second position.

As shown in FIGS. 3 and 4, the specimen retaining panel 12 is disposed between the rear panel 14 and the cover panel 16 when the blood collection card 10 is in the closed configuration. The flap 24 engages the cover panel 16 and maintains the blood collection card 10 in the closed configuration. The cover panel 16 covers the absorbent insert 32 to protect the blood sample 38 from becoming contaminated or otherwise damaged. In the closed configuration, the blood collection card 10 may safely be sent to a testing center. At the testing center, the absorbent insert 32 impregnated with the blood sample 38 can be easily removed from the blood collection card 10 by a technician. The blood sample 38 may then be eluted from the absorbent insert 32 and analyzed.

Figure 5:
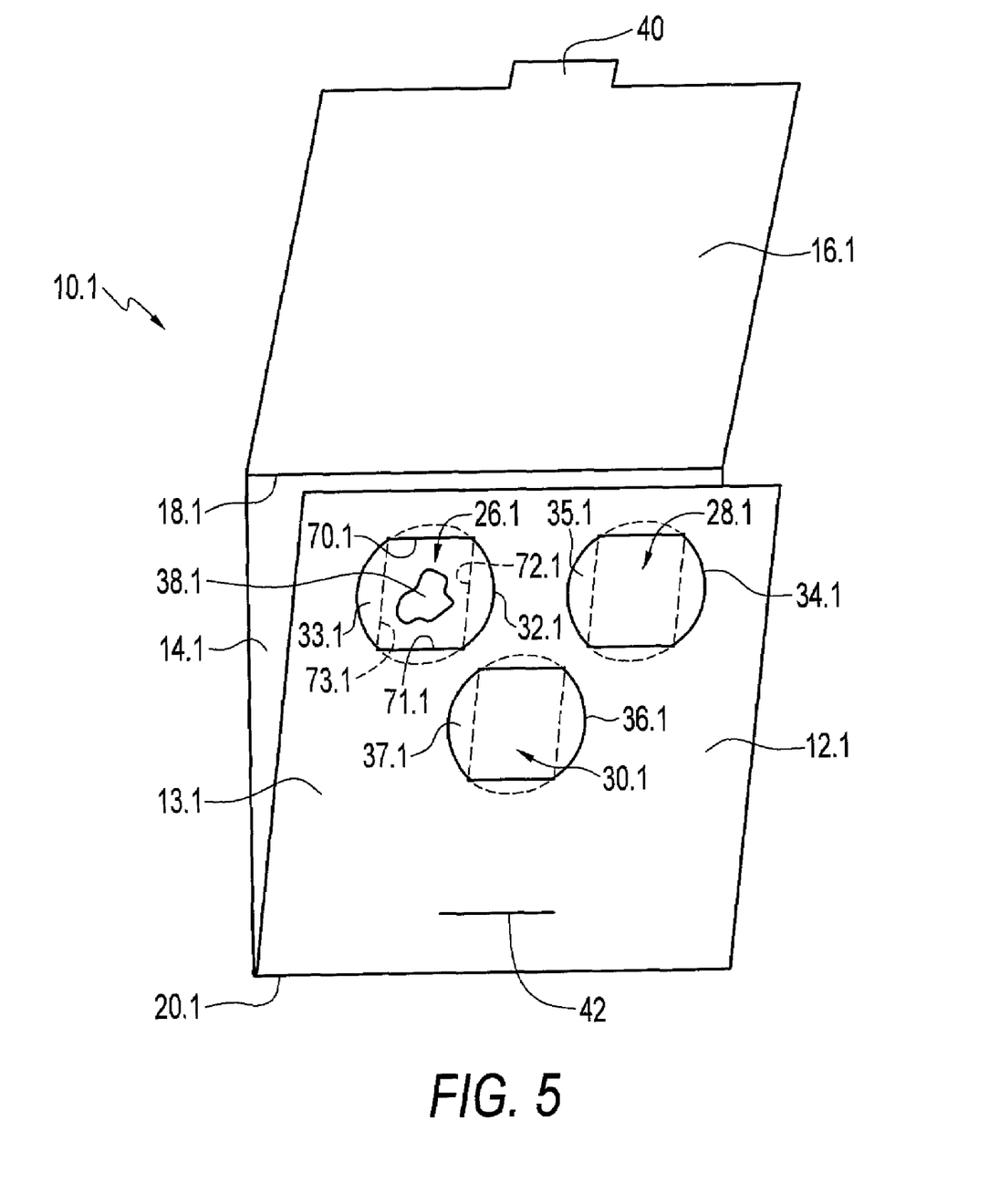
FIG. 5 is a front perspective view of a biological specimen collection card, according to a second embodiment, shown in an open configuration.
Figure 6:
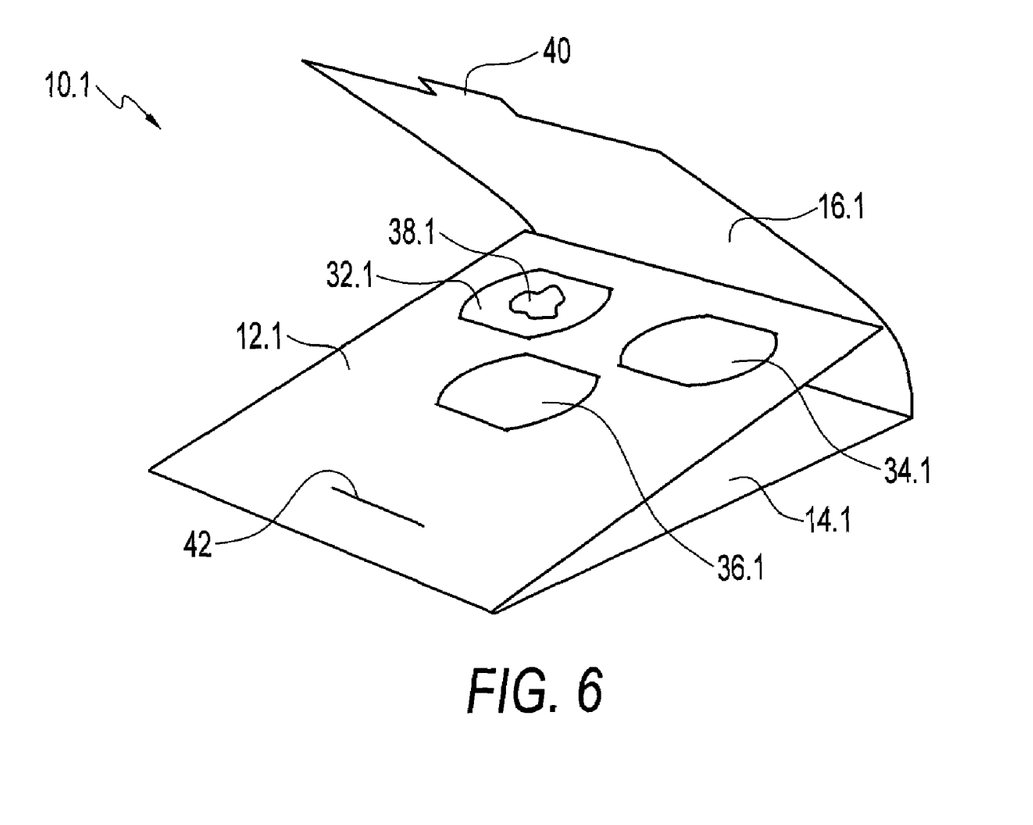
FIG. 6 is a side perspective view of the biological specimen collection card of FIG. 5 shown in the open configuration.
Figure 7:
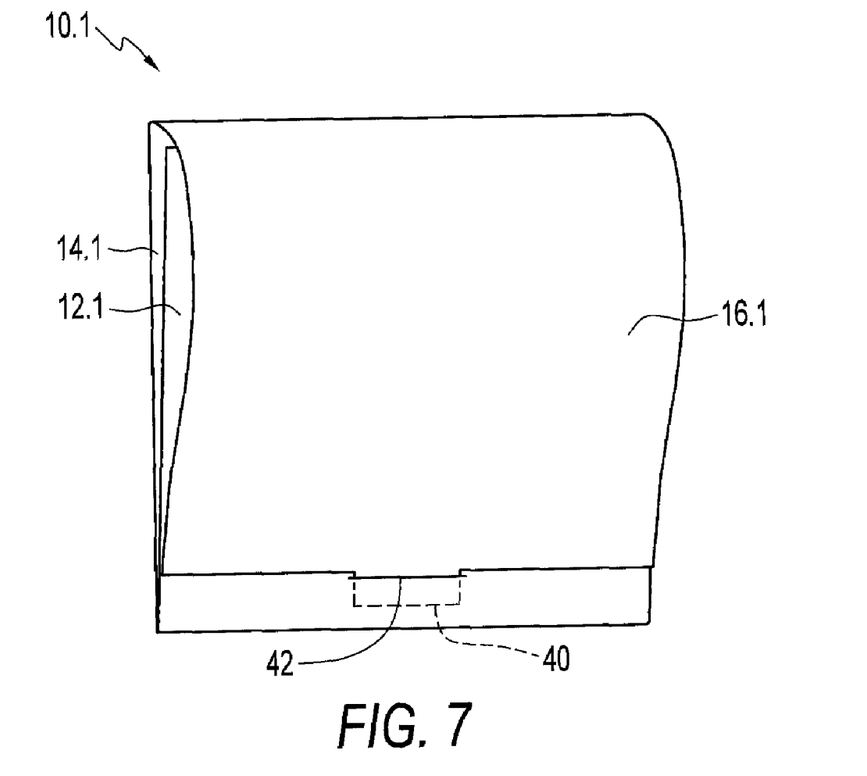
FIG. 7 is a front perspective view of the biological specimen collection card of FIG. 5 shown in a closed configuration.
Figure 8:
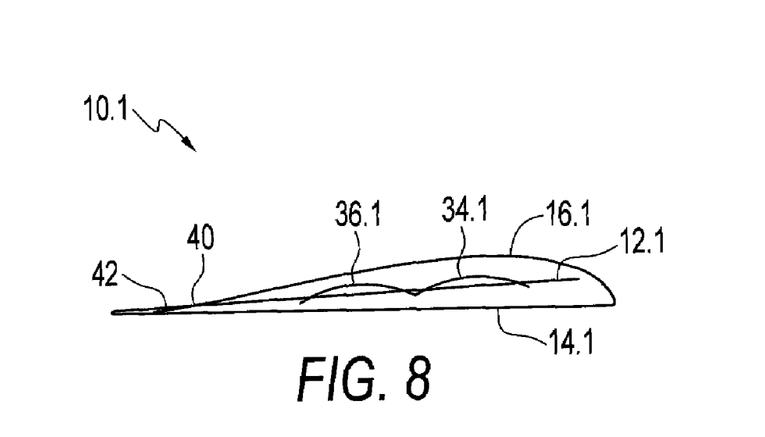
FIG. 8 is a side elevation view of the biological specimen collection card of FIG. 5 shown in the closed configuration.

Referring now to FIGS. 5 to 8, a blood collection card 10.1 is shown according to a second embodiment of the invention. In FIGS. 5 to 8 like parts have been given like reference numerals as in FIGS. 1 to 4 with the additional numerical designation ".1". The blood collection card 10.1 is movable between an open configuration and a closed configuration. FIGS. 5 and 6 show the blood collection card 10.1 in the open configuration. FIGS. 7 and 8 show the blood collection card 10.1 in the closed configuration.

Referring back to FIG. 5, the blood collection card 10.1 generally comprises a specimen retaining panel 12.1, a rear panel 14.1, and a cover panel 16.1. The rear panel 14.1 has a first edge 18.1 and a second edge 20.1 opposite to the first edge 18.1. The cover panel 16.1 is connected to the first edge 18.1 of the rear panel 14.1. The specimen retaining panel 12.1 is connected to the second edge 20.1 of the rear panel 14.1. In this example, there is a tab 40 disposed on the cover panel 16.1 and a slit 42 in the specimen retaining panel 12.1. Openings 26.1, 28.1, and 30.1 in the specimen retaining panel 12.1 retain absorbent inserts 32.1, 34.1, and 36.1, respectively.

In this example, the openings 26.1, 28.1, and 30.1 are quadrilateral and the absorbent inserts 32.1, 34.1, and 36.1 are circular. However, in other embodiments, the openings and inserts may assume other shapes. As shown for one of the openings 26.1, the opening 26.1 has a first pair of opposed edges 70.1 and 71.1 and a second pair of opposed edges 72.1 and 73.1. The corresponding absorbent insert 32.1 engages opposed edges 70.1 and 71.1 of the opening 26.1. When retained in the openings, each absorbent insert is exposed on both sides of the specimen retaining panel 12.1, i.e. both sides of each absorbent insert is exposed. In FIG. 5, only a first side 13.1 of the specimen retaining panel 12.1 and a first side 33.1, 35.1, and 37.1 of each absorbent insert 32.1, 34.1, and 36.1, respectively, is shown. A second side of the specimen retaining panel 12.1 and a second side of each absorbent insert are opposite to the first sides thereof Each absorbent insert 32.1, 34.1, and 36.1 may be impregnated with a blood sample. In this example, only one of the absorbent inserts 32.1 is impregnated with a blood sample 38.1.

The absorbent inserts 32.1, 34.1, and 36.1 are comprised of materials to suit the requirements of a particular application. For example, the absorbent inserts 32.1, 34.1, and 36.1 may be formed from a material designed to retain a high sample volume. Alternatively, the absorbent inserts 32.1, 34.1, and 36.1 may be formed from a material which selectively retains components of a sample, or the absorbent inserts 32.1, 34.1, and 36.1 may be impregnated with a stabilizer or diagnostic reagent. This flexibility in selecting the type of insert used allows the blood collection card 10.1 to be used in a variety of applications. Suitable inserts are available from the Whatman International Ltd., of 27 Great West Road, Brentford, Middlesex, United Kingdom TW8 9BW.

As best shown in FIG. 6, when the blood collection card 10.1 is in the open configuration, the specimen retaining panel 12.1 is angularly spaced apart from the rear panel 14.1 exposing both sides of each absorbent insert 32.1, 34.1, and 36.1 to the environment. This facilitates drying of the blood sample 38.1. This is an important feature because drying of the blood sample 38.1 imparts stability to components of the blood sample 38.1 that are measured during analysis. When the blood sample 38.1 is dry, the cover panel 16.1 is moved from a first position shown in FIG. 6 to a second position shown in FIG. 7. The blood collection card 10.1 is in the open configuration when the cover panel 16.1 is in the first position, and the blood collection card 10.1 is in the closed configuration when the cover panel 16.1 is in the second position.

As shown in FIGS. 7 and 8, the specimen retaining panel 12.1 is disposed between the rear panel 14.1 and the cover panel 16.1 when the blood collection card 10.1 is in the closed configuration. The slit 42 receives the tab 40 and maintains the blood collection card 10.1 in the closed configuration. The cover panel 16.1 covers the absorbent insert 32.1 to protect the blood sample 38.1 from becoming contaminated or otherwise damaged. In the closed configuration, the blood collection card 10.1 may safely be sent to a testing center. At the testing center, the absorbent insert 32.1 impregnated with the blood sample 38.1 can be easily removed from the blood collection card 10.1 by a technician. The blood sample 38.1 may then be eluted from the impregnated absorbent insert 32.1 and analyzed.

Figure 9:
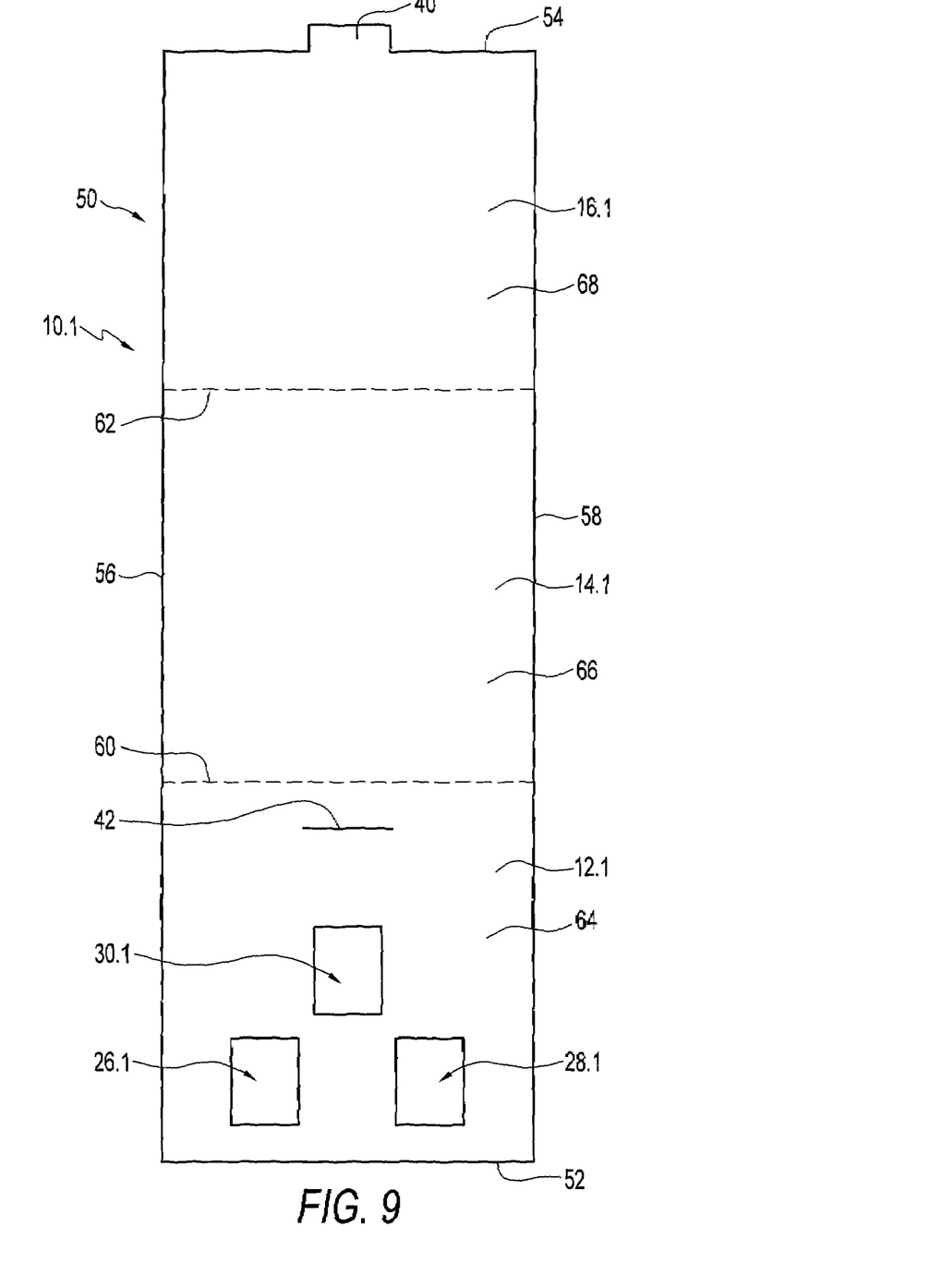
FIG. 9 is a plan view of a blank used to form the biological specimen collection card of FIG. 5.

Referring now to FIG. 9, a blank 50 used to form the blood collection card 10.1 of FIGS. 5 to 8 is shown. The blank 50 has a first end 52 and a second end 54 opposite to the first end 52. First and second edges 56 and 58 of the blank 50 extend between the ends 52 and 54 thereof. The first edge 56 of the blank 50 is opposite to the second edge 58 of the blank 50. First and second lines of weakening 60 and 62 extend between the edges 56 and 58 of the blank 50. The first line of weakening 60 is spaced apart from the second line of weakening 62.

A first portion 64 of the blank 50, which corresponds to the specimen retaining panel 12.1 of the blood collection card 10.1, is defined between the first end 52 of the blank 50 and the first line of weakening 60. A second portion 66 of the blank 50, which corresponds to the rear panel 14.1 of the blood collection card 10.1, is defined between the first line of weakening 60 and the second line of weakening 62. A third portion 68 of the blank 50, which corresponds to the cover panel 16.1 of the blood collection card 10.1, is defined between the second line of weakening 62 and the second end 54 of the blank 50. Openings 26.1, 28.1, and 30.1 for retaining the absorbent inserts (not shown in FIG. 9) are disposed in the first portion 64 of the blank 50. The tab 40 is disposed at the first end 52 of the blank 50 and the slit 42 is disposed near the first line of weakening 60 in the first portion 64 of the blank 50. The blank 50 is folded along the lines of weakening 60 and 62 and absorbent inserts 32.1, 34.1, and 36.1 are positioned in the openings 26.1, 28.1, and 30.1 to form the blood collection card 10.1 which is best shown in FIG. 6.

It will be understood by a person skilled in the art that other embodiments of the invention may employ other means for maintaining the blood collection card in the closed configuration. For example, an adhesive material may be used to maintain the blood collection card in the closed configuration.

It will further be understood by a person skilled in the art that the term "rear" as used herein is used in relation to position of the blood collection cards 10 and 10.1 as shown in FIGS. 1 and 5, respectively.

It will still further be understood by a person skilled in the art that many of the details provided above are by way of example only and are not intended to limit the scope of the invention which is to be determined with reference to the following claims.

What is claimed is:

1. A biological specimen collection card for collecting and transporting a biological specimen, the collection card being movable between an open configuration in which the biological specimen is exposed and a closed configuration in which the biological specimen is covered, the collection card comprising:
    an absorbent insert which is to be impregnated with the biological sample;
    a specimen retaining panel having a first side, a second side and an opening extending therethrough, the opening having a first pair of opposed edges and a second pair of opposed edges, first opposite edge portions of the absorbent insert extending past the first pair of opposed edges of the opening in the specimen retaining panel on the first side of the specimen retaining panel so as to overlay the first side of the specimen retaining panel, and second edge portions of the absorbent insert extending past the second pair of opposed edges of the opening in the specimen retaining panel so as to overlay the second side of the specimen retaining panel, such that a central portion of the absorbent insert is exposed on both the first side of the specimen retaining panel and the second side of the specimen retaining panel, and the absorbent insert is releasably retained in the opening;
    a rear panel angularly spaced apart from the specimen retaining panel when the collection card is in the open configuration to facilitate drying of the biological specimen; and
    a cover panel opposite the rear panel, the cover panel movable between a first position and a second position, the collection card being in the open configuration when the cover panel is in the first position, the collection card being in the closed configuration when the cover panel is in the second position, and the cover panel covering the absorbent insert when the absorbent insert is retained in the opening and the collection card is in the closed position.

2. The biological specimen collection card as claimed in claim 1 wherein the absorbent insert is retained in the opening.

3. The biological specimen collection card as claimed in claim 1 wherein the specimen retaining panel is disposed between the cover panel and the rear panel when the collection card is in the closed configuration.

4. The biological specimen collection card as claimed in claim 1 further including a flap, the flap engaging the cover panel when the cover panel is in the second position to maintain the collection card in the closed configuration.

5. The biological specimen collection card as claimed in claim 1 further including a tab and a slit, the slit receiving the tab when the cover panel in the second position to maintain the collection card in the closed configuration.

6. The biological specimen collection card as claimed in claim 1 further including a web connecting the cover panel to the rear panel.

7. The biological specimen collection card as claimed in claim 1 wherein the collection card is a blood collection card.

8. The biological specimen collection card as claimed in claim 7 wherein the biological specimen is a blood sample.

9. The biological specimen card as claimed in claim 1 wherein the opening is a quadrilateral opening.

10. The biological specimen card as claimed in claim 1 wherein the absorbent insert is circular.

\* \* \* \* \*

UNITED STATES PATENT AND TRADEMARK OFFICE
CERTIFICATE OF CORRECTION

PATENT NO. : 7,976,792 B2
APPLICATION NO. : 11/755605
DATED : July 12, 2011
INVENTOR(S) : Ally Shivji It is certified that error appears in the above-identified patent and that said Letters Patent is hereby corrected as shown below:

IN THE CLAIMS:

Column 6, In claim 1 replace "position" with "configuration" at the end of line 29 so that lines 28-29 read "...and the collection card is in the closed configuration".

Signed and Sealed this
Third Day of January, 2012

David J. Kappos
*Director of the United States Patent and Trademark Office*